United States Patent
Monrabal Bas

(10) Patent No.: US 8,071,714 B2
(45) Date of Patent: Dec. 6, 2011

(54) METHOD FOR SEPARATING AND PURIFYING CRYSTALLISABLE ORGANIC COMPOUNDS

(75) Inventor: Benjamín Monrabal Bas, Parque Tecnolóico de Valencia (ES)

(73) Assignee: Polymer Characterization, S.A., Valencia (ES)

( * ) Notice: Subject to any disclaimer, the term of this patent is extended or adjusted under 35 U.S.C. 154(b) by 29 days.

(21) Appl. No.: 12/282,921

(22) PCT Filed: Mar. 15, 2006

(86) PCT No.: PCT/ES2006/000128
§ 371 (c)(1),
(2), (4) Date: Nov. 18, 2009

(87) PCT Pub. No.: WO2007/104804
PCT Pub. Date: Sep. 20, 2007

(65) Prior Publication Data
US 2010/0056744 A1    Mar. 4, 2010

(51) Int. Cl.
C08G 64/00 (2006.01)
C08G 63/02 (2006.01)
(52) U.S. Cl. .................... 528/502 R; 526/348; 530/344; 530/412
(58) Field of Classification Search .................. 526/348; 530/344, 412
See application file for complete search history.

(56) References Cited

U.S. PATENT DOCUMENTS 5,008,204 A * 4/1991 Stehling .......................... 436/85
5,222,390 A    6/1993 Monrabal

FOREIGN PATENT DOCUMENTS

EP            0327368        8/1989
WO    WO 2004/034047    4/2004

OTHER PUBLICATIONS

Soares et al. "Temperature rising elution fractionation of linear polyolefins." *Polymer*. vol. 36. No. 8. 1995. pp. 1639-1654.
Xu et al. "Application of Temperature rising elution fractionation in polyolefins." *European Polymer Journal*. vol. 36. 2000. pp. 867-878.
Desreux et al. "Fractionnement par extraction du polythene." *Bull. Soc. Chim. Velg.* vol. 59. 1950. pp. 476-489.—English Abstract provided.
Monrabal. "Temperature Rising Elution Fractionation and Crystallization Analysis Fractionation." *Encyclopedia of Analytical Chemistry. John Wily & Sons*. 2000. pp. 1-20.
Shirayama et al. "Distribution of Short-Chain Branching in Low-Density Polyethylene." *J. of Polymer Science. Part A*. vol. 3. 1965. pp. 907-916.
Tung. "Fractionation of Synthetic Polymers: Principles and Practices." *Ed. Marcel Dekker Inc. New York*. 1977. pp. 92-93, 102-103, 106-107, 344-345, 498-501, 514-515, 530-531.
Wild et al. "Development of High Performance Tref. For Polyolefin Analysis." *T. C. Chung. Plenum Press. New York*. 1993. pp. 147-157.

* cited by examiner

*Primary Examiner* — Terressa Boykin
(74) *Attorney, Agent, or Firm* — Merchant & Gould P.C.

(57) ABSTRACT

The invention relates to a process for separating and/or purifying organic compounds susceptible to crystallization by means of crystallizing and dissolving comprising the following steps:
  a) depositing the composition in the head of a separation and/or crystallization column;
  b) crystallizing by means of a cooling gradient;
  c) pumping the solvent at optimal flow rate Fc;
  d) entraining the components while they are not crystallized to the end of the column;
  e) stopping the pumping of the solvent until reaching the lowest temperature of the interval established by the cooling gradient;
  f) heating the column;
  g) beginning new pumping by means of applying flow rate Fe;
  h) collecting the eluates; and
  i) detecting by means of detectors.

17 Claims, 3 Drawing Sheets

METHOD FOR SEPARATING AND PURIFYING CRYSTALLISABLE ORGANIC COMPOUNDS

This application is a National Stage Application of PCT/ES2006/000128, filed 15 Mar. 2006 and which applications is incorporated herein by reference and a claim of priority is made.

FIELD OF THE INVENTION

The present invention is comprised within separation and purification techniques by means of the use of crystallization and dynamic dissolution processes. The present invention additionally relates to a process for separating and purifying compounds with crystallization capacity and particularly for polyolefins, proteins, peptides, fatty acids . . .

STATE OF THE ART

Crystallization is the simplest and most effective technique for purifying solid organic compounds. It consists of dissolving an impure solid in the lowest possible amount of suitable solvent under heat. In these conditions a saturated solution is generated which, upon cooling, becomes oversaturated, causing crystallization. In the crystallization process the molecules which are in solution are in equilibrium with the molecules forming part of the crystal lattice.

The high degree of arrangement of a crystal lattice excludes the participation of impurities therein. It is therefore suitable for the cooling process to occur slowly such that the crystals are formed little by little and the slow growth of the crystal lattice excludes impurities or other components. If the solution is cooled very quickly, the impurities can be trapped in the crystal lattice. L. H. Tung, Fractionation of Synthetic Polymers, Ed. Marcel Dekker Inc. New York, 1977

The processes for separating and/or purifying by means of crystallization and precipitation are well known in the literature. Among these processes, those for separating and/or purifying by crystallization and precipitation widely applied in the industry and also applied as analytical mixture characterization techniques must be pointed out.

In Temperature Rising Elution Fractionation (TREF) processes, V. Desreux and M. L. Spiegels, Bull. Soc. Chim. Belg., 59, 476 (1950); K. Shirayama, T. Okada and S. I. Kita, J. Polym. Sd. part A, 907 (1965) and L. Wild and C. Blatz, New Advances in Polyolefins, T. Chung, Ed., Plenum Press, New York, pp. 147-157, 1993, show that the physical separation of the fractions of a previously crystallized mixture in a column packed with inert spheres, widely described in the state of the art, is obtained by dissolving the components as the temperature rises and while a solvent is pumped through the column. TREF analysis is rather slow and usually requires between 10 and 20 hours per sample; analysis are still carried out in the industry which last more than a day. Preparative fractionation by TREF is even slower and usually requires several days to physically separate a sample into several fractions.

Another known method in the state of the art is CRYSTAF (Crystallization Analysis Fractionation) developed by B. Monrabal, Crystallization Analysis fractionation, U.S. Pat. No. 5,222,390 (1991), which describes a new process of obtaining analytical separation during crystallization by taking aliquot amounts of the solution being crystallized in an agitated vessel through a filter and analyzing their concentration, whereby generating an accumulated curve of the crystallization curve and hence a composition curve. This technique provides a much higher analysis rate than conventional TREF; nevertheless, the analysis of 5 samples still requires about six hours for example.

The TREF and CRYSTAF techniques have a similar separation power for most compounds with crystallization capacity, as can be seen in B. Monrabal, Encyclopedia of Analytical Chemistry, John Wiley & Sons, 2000 pages 8074-8094, as they are based on the same thermodynamic principles. The problem with the previously described processes is that despite having good results, the duration of such processes is very high, and this furthermore makes the process substantially more expensive. For this reason great interest has been shown in recent years in searching for and developing separation and purifications processes that are not associated with these intrinsic problems, and therefore the time is substantially reduced, increasing the separation and analysis rate without losing resolution.

For this reason the main object of the present invention is to develop a process for separating and/or purifying by means of crystallization and precipitation such that wait times are reduced and the rate of the process is accordingly increased, without substantially affecting the quality of the result thereof. In this sense no processes have been found in the state of the art which use columns packed with inert particles having diameters comprised between 5 and 200 microns for cooling conditions in the case of crystallization and heating conditions in the case of elution which are greater than or equal to 1° C./min, compared to what has been described in the state of the art, in which the applied conditions were always less than 1° C./min. It is therefore also object of the present invention applying said conditions to the new process described in the invention and also to the TREF process described in the state of the art in which said conditions were never applied because it seemed unlikely that they would work for this high analysis rate methodology.

DESCRIPTION OF THE INVENTION

The object of the present invention is to provide a new process for separating and/or purifying organic compounds susceptible to crystallization by means of crystallizing and dissolving, by means of which the crystallizable compounds of a mixture are separated at a higher resolution and rate (high throughput). In relation to the state of the art, the present invention presents the novelty of carrying out the crystallization in a dynamic manner, compared to the already known static manner.

The process object of the present invention is characterized in that it comprises the following steps:
  depositing the composition of the organic compounds (the components of which crystallize at different temperatures) to be separated and/or purified in the head of a chromatography column which is packed with inert type spheres.
  beginning the crystallization process by means of establishing a temperature gradient between 200-(−)50° C. (ΔT=Ti−Tf), for example, which generates a cooling gradient (Cr measured in ° C./min).
  establishing pumping of the normally polar type solvent if the components of the composition have a polar nature, or an apolar type solvent if the components are apolar, at a certain flow rate (Fc) which is comprised between 0.01-0.5 ml/min, depending on the interstitial volume (Vi) of the column which is normally comprised between 0.1-10 ml in the analytical field. In semi-industrial or industrial separation or purification processes, these values must be adapted to the size of the mixture to be separated.

At this point it is necessary to clarify that the flow rate Fc must be the optimal flow rate and that the following formula must be taken into account to calculate such rate:

$$Fc = Vi/tc, \text{ where tc or crystallization time is } tc = \frac{T/Cr}{}$$

Flow rates under the optimal flow rate would not make use of the separation potential in the column and flow rates above the optimal flow rate would elute non-crystallized components out of the column.

The following step in the process is to gradually entrain the components while they are not crystallized to the end of the column.

Once crystallization has ended, upon reaching the final temperature Tf and all the components have presumably been crystallized, pumping of the solvent is stopped or ended.

The column is heated.

A new elution flow rate Fe is applied to gradually elute the different crystallized components.

The eluate is collected; and/or

The eluate is detected by means of at least 1 concentration detector but other in-line viscometer, light scattering or infrared or IR type detectors can also be added.

In a particular embodiment of the present invention the column heating step is carried out as shown in FIG. 1 by means of instant column heating up to a temperature above the dissolving temperature solution (Td) of all the components, followed by pumping of the solvent at a flow rate Fd at constant temperature and finally obtaining the elution of all the separated components that were anchored to the column during crystallization.

According to another particular embodiment of the present invention, the column heating step is carried out as shown in FIG. 2 by means of establishing a temperature or heating gradient Hr normally between 0.01 and 10° C./M and in a temperature range normally between −50 and +200° C., followed by pumping at an elution flow rate Fe normally between 0.1 and 10 ml/m for analytical applications, and finally obtaining the separation which, in this case, is higher than the conventional methods, such as TREF. The level of improvement will depend on the Vi (interstitial volume) of the column and its geometry so that the effects of sample diffusion are reduced, which will finally result in the separation additionally obtained in the first dynamic crystallization step.

According to a preferred embodiment, the previously described process could have associated thereto a longitudinal thermal field which moves in the "suitable" direction, i.e. from the opening of the column to the end of the column or tail, being in this case a cooling gradient for bringing about crystallization, which process is referred to as cooling, and from the tail to the opening, being in this case a heating gradient for bringing about the elution of the components, which process is referred to as heating. The separation of components obtained in dynamic crystallization (dynamic crystallization being understood as all the steps of the new process, up to column heating without including this last step) and in elution would be even further increased by means of this process.

According to another preferred embodiment as shown in FIG. 4, the process described in the present invention can be repeated n times, n being comprised between 2 and 100, cyclically by carrying out multiple heating-cooling cycles such that the separation and purification potential is improved, requiring to that end the use of columns with a greater interstitial volume and preferably large lengths, normally between 0.2 and 100 meters.

The new process described in the present invention uses columns preferably packed with small sized inert particles having diameters comprised between 5 and 200 microns. In the case of crystallization, it is subjected to cooling conditions by means of a cooling gradient Cr. In the case of elution, it is subjected to heating conditions by means of a heating gradient Hr. In both cases for this new process described in the present invention specification, both gradients (Cr and Hr) may comprise any numerical range.

According to another preferred embodiment, columns packed with small sized inert particles, having diameters comprised between 5 and 200 microns, can be applied in the TREF process described in the state of the art for conditions in which the cooling gradient and heating gradient are equal to or greater than 1° C./minute, given that these conditions had never been defined in the state of the art for this process (TREF) because it seemed unlikely that they would work for this methodology, and surprisingly good results are thus obtained at a high analysis rate with little effect on the loss of resolution.

Another aspect of the present invention is the process for separating and/or purifying any type of substance susceptible to crystallization. According to a preferred embodiment, the use of the process is mainly for polymers susceptible to crystallization and even more preferably for proteins, peptides, polyolefins, fatty acids . . .

Several preferred embodiments according to the present invention are described below with non-limiting examples in order to understand such invention.

BRIEF DESCRIPTION OF THE DRAWINGS

The present invention will be described below with the aid of the following figures.

DETAILED DESCRIPTION OF AND EMBODIMENT

EXAMPLE 1

To demonstrate the process described in the present invention, by means of which dynamic crystallization (with pumping of the solvent during crystallization) was carried out, a mixture of two polyethylene resins having different crystallinities was separated.

The sample dissolved in trichlorobenzene was deposited in the head of a column having an inner diameter of 1 mm and packed with 90-125μ steel particles, and the following cooling gradient was carried out with the following test conditions:

$$\Delta T = (100 \rightarrow 30)°\ C.\ at\ Cr=2°\ C./min\ and\ with\ a\ flow\ rate\ of\ Fc=0.02\ ml/min$$

When the dynamic crystallization ended and the flow rate was stopped, the column temperature instantly increased up to 160° (which dissolves the two components of the mixture) and after 5 minutes solvent is pumped through the column at F=0.1 ml/min, passing through an infrared detector functioning as a concentration detector.

Figure 6:
FIG. 6 is a comparative example of the effect shown in the absence or in the presence of dynamic crystallization.

The obtained result is 2 separate peaks, as shown in FIG. 6a.

If the same experiment is repeated with the same sample, the same column and the same analytical conditions but with static crystallization (without pumping the solvent during crystallization), i.e. crystallizing:

$$\Delta T=(100\rightarrow 30)C.°\ at\ Cr=2°/min\ without\ flow\ rate$$

and instantly heating to 160° C. and after 5 minutes beginning the pumping at F=0.1 ml/min, no separation of the components of the mixture will be obtained, as can be observed in FIG. 6b.

Therefore, the effect of dynamic crystallization compared to the effect of static crystallization previously described in the state of the art is demonstrated by means of this example.

EXAMPLE 2

Figure 7:
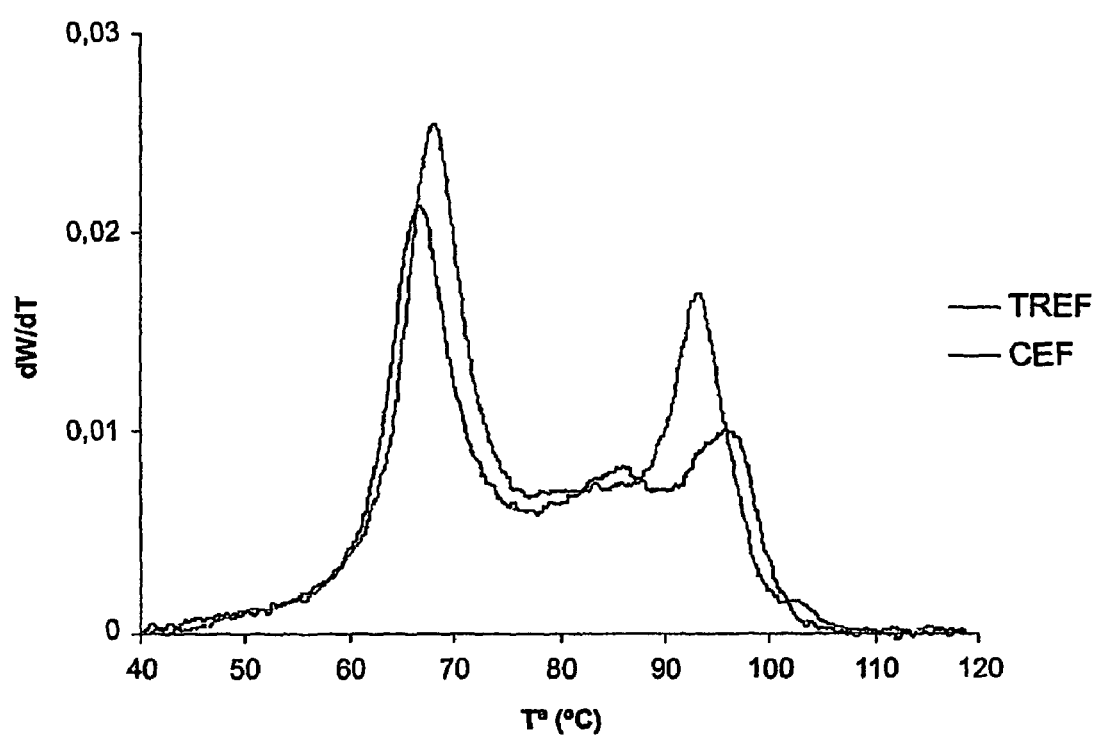
FIG. 7 is the graphic representation of a comparative example between the new claimed process and the TREF process.

According to the process described in the present invention and as is shown in FIG. 7, the present example demonstrates the possibility of improving conventional TREF with the new separation process in which a heating gradient and a flow rate are applied in the heating step. Tri-mode analyses are carried out on a sample of polyethylene in a 2 m tube column having an inner diameter of 1 mm and packed with 90-125μ steel particles in TREF mode and according to the new process (with crystallization flow rate Fc) claimed in the present invention in the analytical conditions presented in Table 1:

TABLE 1

|  | TREF | New process with Fc |
| --- | --- | --- |
| Crystallization, range and Cr ° C./m | 100-30° C., 5°/m | 100-30° C., 5° C./m |
| Crystallization flow rate, Fc |  | Fc = 0.05 ml/m |
| Solution, range and Hr ° C./m | 30-120° C., 5°/m | 30-120° C., 5° C./m |
| Elution flow rate, Fe | 0.5 ml/m | 0.5 ml/m |

As can be observed in FIG. 7, the TREF process only resolves two peaks, whereas the new process resolves 3 peaks of the mixture.

EXAMPLE 3

The present example shows the effect of the new conditions for the process described in the present invention compared to the conditions used in the state of the art of TREF.

Figure 1:
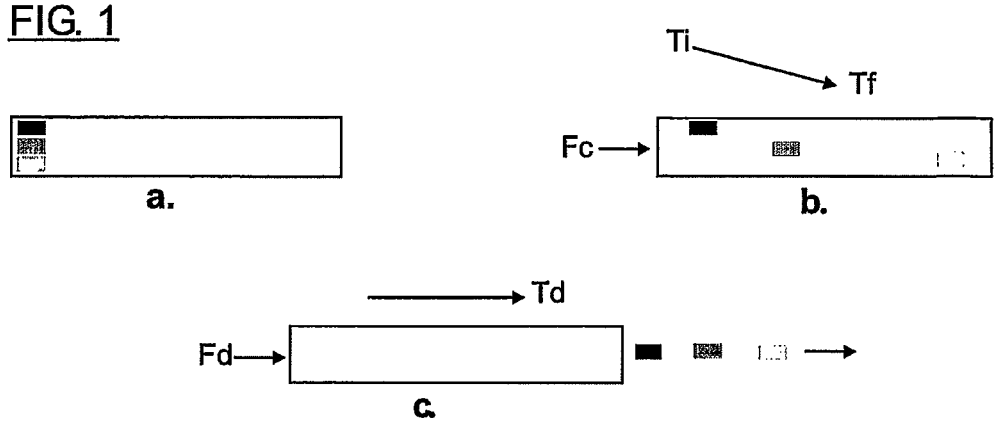
FIG. 1 is a diagram of the separation and/or purification process which uses, after dynamic crystallization with pumping of the solvent during the entire crystallization process, subsequent instant column heating up to a temperature above the dissolution temperature of all the components, with subsequent elution of the samples. It can be observed in FIG. 1 how the mixture to be separated, in this case 3 components crystallizing at three different temperatures (FIG. 1*a*), has been deposited in the column. Once crystallization begins, between two set temperatures Ti and Tf (such that ΔT=Ti−Tf) and with a cooling gradient Cr in ° C./m, pumping of the solvent at a certain flow rate Fc in ml/m begins, which solvent will gradually entrain the components while they are not crystallized towards the end of the column. Upon reaching temperature Tf, the components will be physically separated inside the column as shown in FIG. 1*b*. This physical separation in crystallization is in and of itself a new process for physically obtaining the separation of components by crystallization which would be completed upon ending the pumping of the solvent upon reaching Tf, followed by column heating up to a temperature above the dissolution temperature of all the components, Td, when a new pumping of the solvent at flow rate Fd in isothermal conditions would begin to obtain the elution of all the components which were anchored in the column during crystallization separately over time, as described in FIG. 1*c*.
Figure 2:
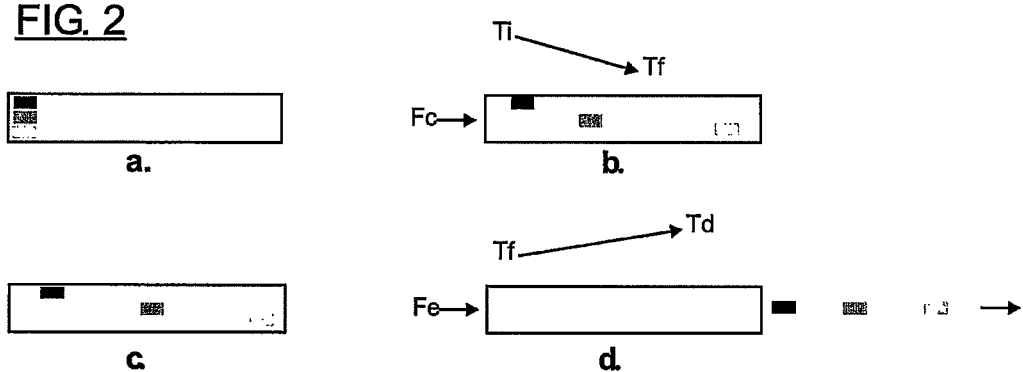
FIG. 2 is a diagram of the separation and/or purification process in which, after crystallization, it is subjected to a temperature or heating gradient with subsequent elution of the samples. Based on the same process as in FIG. 1, when crystallization ends and flow rate, Fc, has been stopped at temperature Tf (see FIG. 2c), a heating gradient Hr and new pumping at elution flow rate Fe begins, as described in FIG. 2d, whereby obtaining an additional separation.
Figure 3:
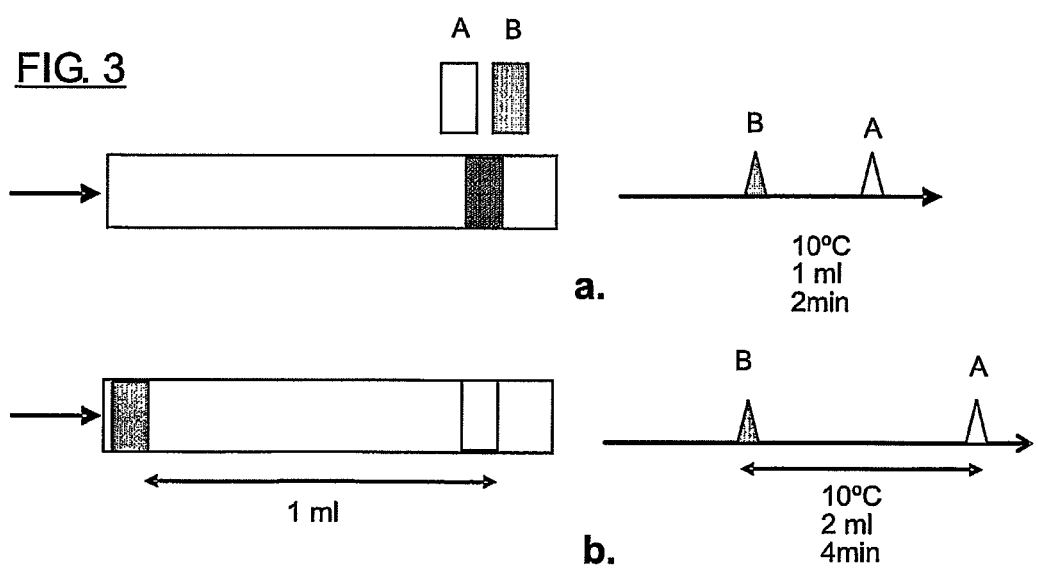
FIG. 3 shows a comparative diagram between the process described in the present invention, in which a heating gradient is provided, and the process described in the state of the art, TREF. The improvement obtained in relation to simple separation processes can be conceptually quantified (FIG. 3b). In this case, the process starts by using a mixture of two semi-crystalline components A and B which are separated 10° C. in their crystallization or elution temperature. If a separation is carried out by the conventional TREF technique in the following elution conditions: Hr=5° C./min, Fe=0.5 ml/min, and loading the mixture at the end of the column, a separation is obtained such as that which is described in FIG. 3, with a distance between the separated components or peaks of 2 minutes, 10° C. and 1 ml. However, if the separation is carried out using the new process with column heating by means of a heating gradient, initially loading the sample in the head of the column and adding pumping during the crystallization of 1 ml (the flow rate will depend on the crystallization gradient) and if TREF continues to be carried out subsequently in the same direction and in the same Hr and Fe conditions, the separation of the components by means of the new process will have increased to 4 minutes, 2 ml and 10° C., as can be observed in FIG. 3b.
Figure 4:
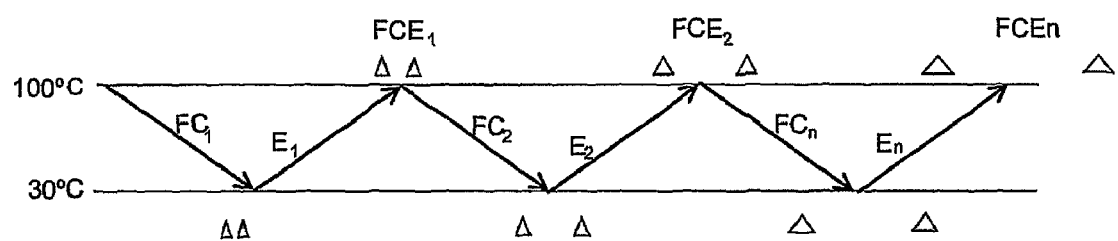
FIG. 4 shows a diagram of carrying out the new process with the application of a temperature gradient or column heating, with subsequent repeated elution carried out cyclically n times after crystallization, where FC is the crystallization process, E is the elution process and FCE is the resultant of FC and E.
Figure 5:
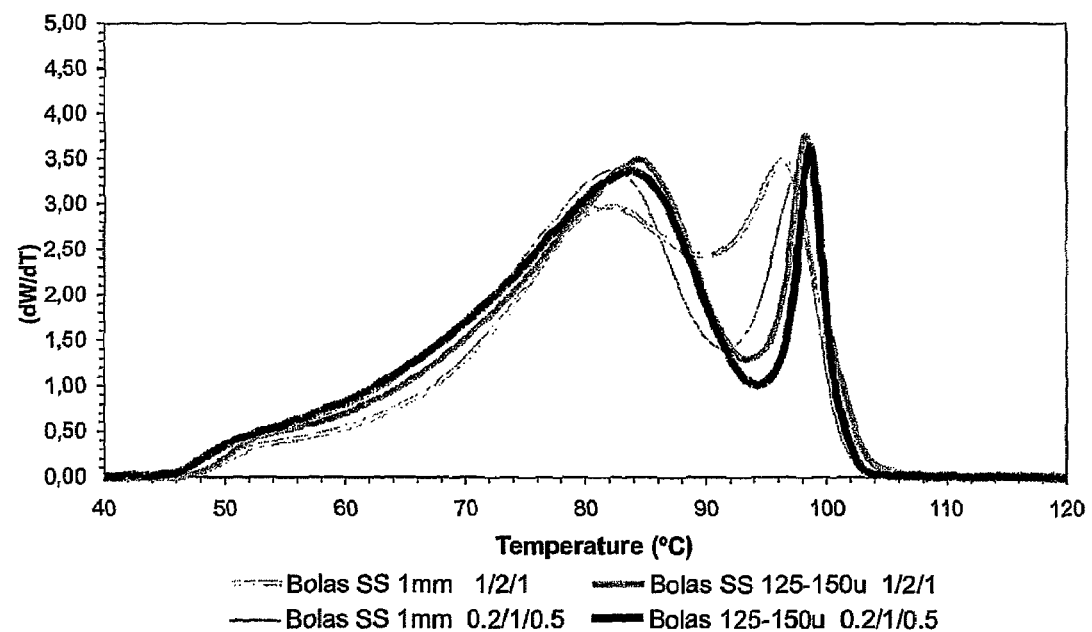
FIG. 5 comparatively shows the improvement presented by the new claimed process for heating and cooling conditions equal to or greater than 1° C./min compared to what is established in the state of the art (TREF).

As can be observed in FIG. 5, the use of particles having a small diameter allows improving the kinetic aspects in crystallization and elution processes in packed columns. The present example comparatively describes the process described in the present invention for four different conditions, as shown in Table 2:

TABLE 2

| Column | Conditions | Cr (° C./min) | Hr (° C./min) | Fc and Fd (ml/min) |
| --- | --- | --- | --- | --- |
| (1) | 1 mm ss spheres | 1 | 2 | 1 |
| (2) | 125-150μ spheres | 1 | 2 | 1 |
| (3) | 1 mm ss spheres | 0.2 | 1 | 0.5 |
| (4) | 125-150μ spheres | 0.2 | 1 | 0.5 |

As can be observed in FIG. 5 and Table 2, the advantages are not significant in slow analysis conditions (Cr and Hr<1° C./min) as can be observed in lines 3 and 4, in the dual-mode analysis of low-density linear polyethylene; however the advantages are very considerable at high cooling and crystallization rates, as is demonstrated in FIG. 5 in lines 1 and 2, thus allowing the use of Cr and Hr conditions equal to or greater than 1° C./min. An increase in the separation and/or purification rate (high throughput) has thus been obtained.

The invention claimed is:

1. A process for separating and/or purifying organic compounds susceptible to crystallization by crystallizing and dissolving, comprising the following steps:
   a) depositing a composition comprising an organic compound susceptible to crystallization in the head of a chromatography column packed with inert type spheres;
   b) crystallizing by a cooling gradient while pumping a solvent at a flow rate Fc between 0.01-0.5 ml/min;
   c) entraining components of the composition while they are not crystallized to the end of the column;
   d) stopping the pumping of the solvent upon reaching the lowest temperature of the interval established by the cooling gradient;
   e) heating the column;
   f) beginning new pumping by applying flow rate Fe;
   g) collecting eluates; and
   h) detecting said organic compounds by at least one concentration detector.

2. A process according to claim 1, wherein in step e), column heating is instant and is above the dissolution temperature of all components.

3. A process according to claim 1, wherein in step e), the column heating is carried out by a heating gradient.

4. A process according to claim 1, wherein the at least one concentration indicator comprises an in-line viscometer, light scattering detector and/or infrared detector.

5. A process according to claim 1, wherein said process comprises a longitudinal thermal field associated to the column.

6. A process according to claim 1, wherein said process is carried out n times cyclically.

7. A process according to claim 6, wherein n is between 2 and 100.

8. A process according to claim 1, wherein the column is packed with inert particles having diameters between 5 and 200 microns.

9. A process according to claim 1, wherein the cooling gradient is equal to or greater than 1° C./minute when said process is for TREF.

10. A process according to claim 1, wherein said process is carried out in columns having an inner diameter equal to or greater than 4 mm.

11. A process according to claim 9, wherein said process is carried out in columns packed with inert particles having a diameter between 5 and 200 microns.

12. A process according to claim 1, wherein the organic compounds susceptible to crystallization are polymers and biological compounds.

13. A process according to claim 12, wherein the polymers are polyolefins.

14. A process according to claim 12, wherein the biological compounds are peptides, proteins and fatty acids.

15. A process according to claim 12, wherein the organic compounds have crystallization potential.

16. A process according to claim 3, wherein said heating gradient is equal to or greater than 1° C./minute when said process is for TREF.

17. A process according to claim 1, wherein the process is a semi-industrial or industrial separation or purification process for organic compounds.

* * * * *